United States Patent
Batistelli

(10) Patent No.: US 7,481,223 B1
(45) Date of Patent: Jan. 27, 2009

(54) SUPPORT HEADBAND FOR OXYGEN SUPPLY TO NOSE

(76) Inventor: Nello Batistelli, 2025 Woodbriar Ct., Fullerton, CA (US) 92831

( * ) Notice: Subject to any disclaimer, the term of this patent is extended or adjusted under 35 U.S.C. 154(b) by 0 days.

(21) Appl. No.: 11/832,628

(22) Filed: Aug. 1, 2007

(51) Int. Cl.
*A61M 11/00* (2006.01)
(52) U.S. Cl. .......................... 128/207.18; 128/DIG. 26
(58) Field of Classification Search ........... 128/207.18, 128/206.11, DIG. 26, 203.22, 204.11
See application file for complete search history.

(56) References Cited

U.S. PATENT DOCUMENTS

| | | | |
|---|---|---|---|
| 858,431 | A | 5/1907 | Allen |
| 2,259,817 | A | 10/1941 | Hawkins |
| 4,665,566 | A | 5/1987 | Garrow |
| 4,739,757 | A | 4/1988 | Edwards |
| 4,742,824 | A * | 5/1988 | Payton et al. .......... 128/207.18 |
| 4,808,160 | A | 2/1989 | Timmons et al. |
| 5,645,058 | A | 7/1997 | Odom |
| 5,687,715 | A | 11/1997 | Landis et al. |
| D479,327 | S * | 9/2003 | Hansen ....................... D24/128 |
| 2004/0025884 | A1 | 2/2004 | McKown |
| 2005/0061326 | A1 | 3/2005 | Payne, Jr. |
| 2005/0121087 | A1 | 6/2005 | Wood |
| 2006/0180151 | A1 | 8/2006 | Rinaldi |

* cited by examiner

*Primary Examiner*—Steven O Douglas
(74) *Attorney, Agent, or Firm*—Kenneth L. Green; Edgar W. Averill, Jr.

(57) ABSTRACT

A personal oxygen supply tubing management system includes a headband for positioning and grasping the tubing. The headband includes a rear tubing entry point, a curved path for grasping the tubing to prevent sliding, and an exit over a patient's ears. The curved path is created by a flap which resides over the tubing and obstructions between the flap and the headband which prevents the tubing from assuming a straight path. For example, the obstructions may be four mutually offset snaps forcing the tubing to assume a curved path to navigate past the snaps. The headband may be worn as a headband alone or may be a headband of a cap or hat. Integrating the oxygen supply tubing management system into a cap, for example a common base ball cap, provides a degree of concealment and reduces or eliminates the embarrassment a patient may experience when wearing an oxygen supply.

10 Claims, 2 Drawing Sheets

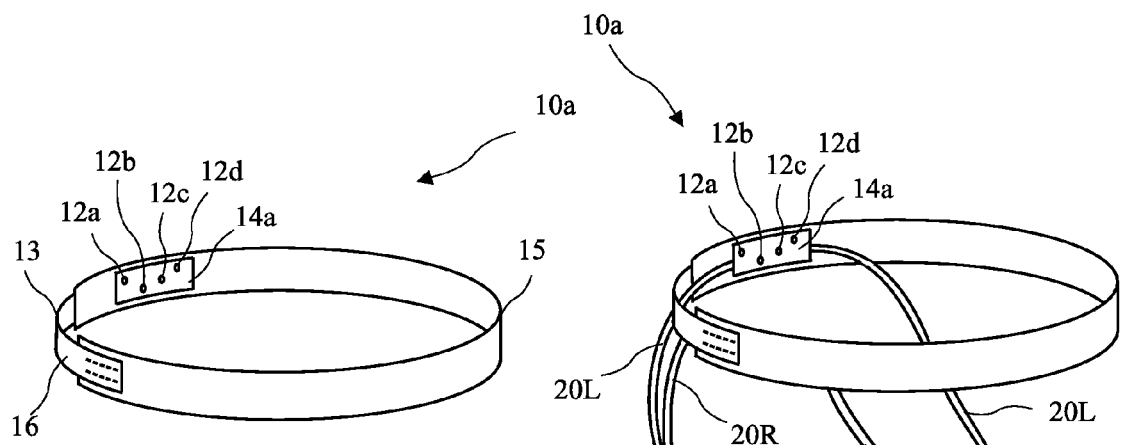
FIG. 1
FIG. 2
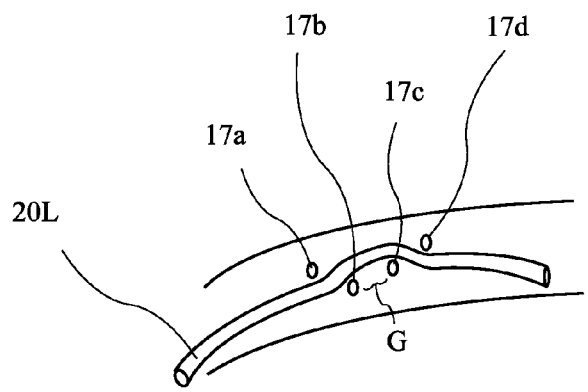
FIG. 2A

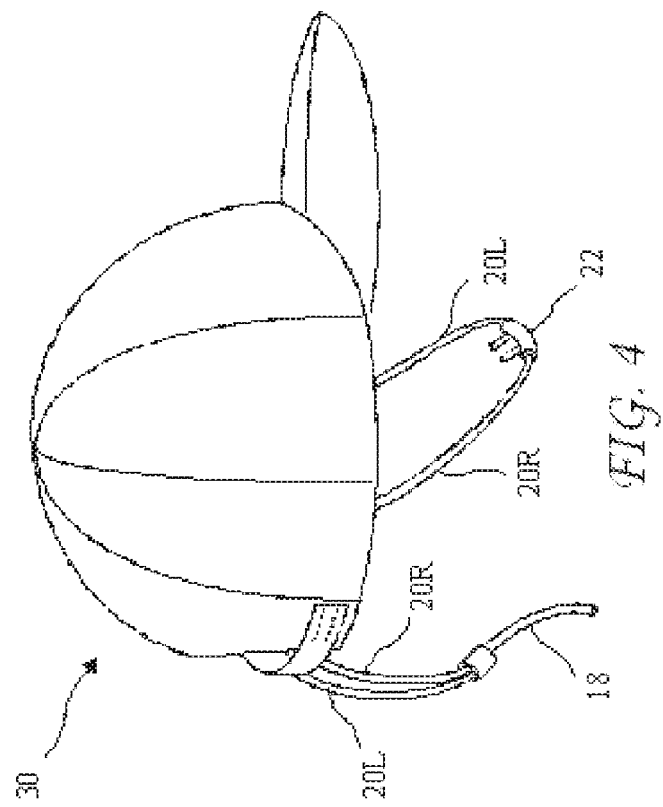
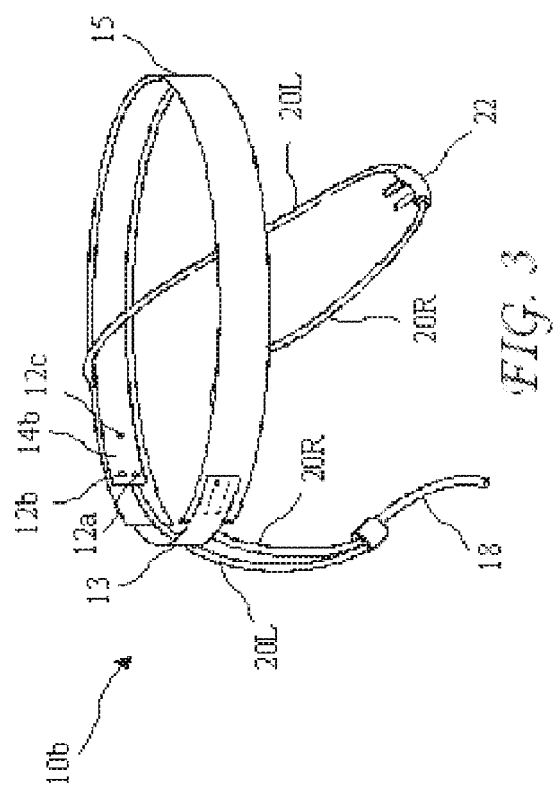

SUPPORT HEADBAND FOR OXYGEN SUPPLY TO NOSE

BACKGROUND OF THE INVENTION

The present invention relates to patient worn oxygen systems and in particular to a headband for managing oxygen lines worn by a patient.

Various physical conditions motivate or require an increased oxygen supply to a patient. In less severe cases, an oxygen mask is not required, and the increased oxygen is provided by a nasal cannula connected to oxygen tubes and worn in or near the entry to the nasal passages. Unfortunately, such tubes may cause discomfort and make sleeping difficult. Further, the tubes are often worn over the ears, along the sides of the face, and under the chin, and cause blisters, irritation, sores, etc.

Although when using known apparatus, the tubes may be initially positioned to provide an adequate oxygen supply and comfortable wearing, unfortunately, one or both tubes often move away from the nasal passages during sleep and result in an inadequate supply of oxygen. Such oxygen reduction may hinder a patient's recovery or even put their life at risk. Further, such oxygen leak over a period of time may result in an oxygen rich environment, especially in a small room. An oxygen rich environment creates a fire risk, and a patient requiring oxygen, and somewhat deprived of oxygen, would find it very difficult to deal with the potential fire.

Additionally, known patient worn oxygen systems are highly visible and often make a patient self conscious.

BRIEF SUMMARY OF THE INVENTION

The present invention addresses the above and other needs by providing a personal oxygen supply tubing management system which includes a headband for positioning and grasping the oxygen supply tubing and position a nasal cannula near a patient's nasal passages. The headband includes a rear tubing entry point, a curved path for grasping the tubing to prevent sliding, and an exit over a patient's ears. The curved path is created by a flap which resides over the tubing and by obstructions between the flap and the headband which prevents the tubing from assuming a straight path and from moving with respect to the headband. For example, the obstructions may be four mutually offset snaps forcing the tubing to assume a curved path to navigate past the snaps. The present invention thus prevents blisters, irritation, and sores resulting from movement of the oxygen tubes, and prevents the nasal cannula from moving away from the entry to the nasal passages. The headband may be worn as a headband alone or may be a headband of a cap or hat. Integrating the oxygen supply tubing management system into a cap, for example a common base ball cap, provides a degree of concealment and reduces or eliminates the embarrassment a patient may experience when wearing an oxygen supply.

In accordance with one aspect of the invention, there are provided oxygen tubes for a personal oxygen supply and headwear for carrying the oxygen tubes. The oxygen tubes and headwear include a nasal cannula, a right oxygen tube connecting an oxygen source to the nasal cannula, a left oxygen tube connecting the oxygen source to the nasal cannula, and a headband. The headband resides around a wearer's head and has a headband front and a headband rear. A right flap resides on a right inside rear portion of the headband and a left flap resides on a left inside rear portion of the headband. At least three snaps hold each flap in position. A right path is provided to carry the right oxygen tube under the right flap and includes a right tube entry towards the headband rear and a right tube exit towards the headband front. A left path is provided to carry the left oxygen tube under the left flap and includes a left tube entry towards the headband rear and a left tube exit towards the headband front. The snaps force the tubes to assume a curve along the paths, thereby holding the tubes.

In accordance with another aspect of the invention, there are provided oxygen tubes for a personal oxygen supply and a cap for carrying the oxygen tubes. The oxygen tubes and cap include a cap top for covering a wearer's head, a cap headband for carrying the cap on the wearer's head and having a headband front and a headband rear, a nasal cannula, and right and left oxygen tubes connecting an oxygen source to the nasal cannula. The cap headband includes a right flap residing on a right inside rear portion of the headband and a left flap residing on a left inside rear portion of the headband. At least three snaps hold each flap in position. A right path is provided for the right oxygen tube under the right flap and includes a right tube entry towards the headband rear and a right tube exit towards the headband front. A left path is provided for the left oxygen tube under the left flap, the left path including a left tube entry towards the headband rear and a left tube exit towards the headband front. The snaps force the tubes to assume a curve along the paths, thereby holding the tubes.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 1 is a headband according to the present invention.

FIG. 2 is the headband with an oxygen tube carried by the headband.

FIG. 2A is a detailed view of the oxygen tube forced into a curved shape by the headband.

FIG. 3 describes an embodiment of the headband according to the present invention.

FIG. 4 is a cap including a headband according to the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

A first headband 10*a* according to the present invention is shown in FIG. 1 and the headband 10*a* is shown carrying a left oxygen tube 20L and a right oxygen tube 20R attached to a nasal cannula 22. The tubes 20L and 20R are preferably connected to an oxygen source to provide a flow of oxygen to a wearer through the nasal cannula 22. Although headbands for carrying oxygen tubes are known, the known headbands allow the tubes to slide forward or rearwards, and result in discomfort or in undesired movement of a nasal cannula, thus depriving a wearer of the needed oxygen. The headband 10*a* has a headband rear 13 and a headband front 15, and may be a separate article, for example, a sweatband or a decorative headband, or the headband may be part of a cap, a hat, or any other headwear.

In order to better hold the tubes 20L and 20R, the headband 10a according to the present invention includes a left flap 14a and a right flap (not shown) opposite the left flap 14a, both flaps reside inside and towards the rear 13 of the headband 10a. The flap 14a is detachable and is preferably held in place by four attachments 12a-12d. The attachments 12a-12d are preferably positioned to hold the flap 14a in place and to allow a wearer to adjust the paths of the tubes 20L and 20R to force the tubes to curve, thereby resisting sliding of the tubes.

The attachments 12a-12d further allow the flap 14a to be detached or lifted away from the headband 10a to allow the tube 20L to be installed into a passage under the flap 14a. Preferably, the flaps are either totally detachable from the headband, or permanently attached along only one edge. Because the oxygen tubes are generally provided as a single unit, it is important to be able to route the tubes without having to thread the tubes through a passage. The attachments may be snaps, patches of Velcro® fastener material, or the like, and are preferably snaps. The right flap is held as described for the left flap 14a.

The attachments 12a-12d of the headband 10a are arranged with the first attachment 12a positioned high and toward the rear of the flap 14a, the second attachment 12b positioned low and ahead of the first attachment 12a of the flap 14a, the third attachment 12c positioned at a medium height and ahead of the second attachment 12b of the flap 14a, and the fourth attachment 12d is positioned high and at a forward end of the flap 14a ahead of the third attachment 12c. While a particular arrangement of the attachments is described in FIG. 2, any arrangement of the attachments which secures the flaps and allows a wearer to force the tubes to follow a curve is intended to come within the scope of the present invention. While the attachments may be arranged in a straight line, such straight arrangement may not hold the flap 14a against the headband, and the attachments preferably are positioned to urge the flaps to lay against the headband for comfortable wearing. The flaps are preferably made of a material having approximately the same stretch as the headband to provide a comfortable fit and a preferred material is leather, leather like material, vinyl, and similar material.

A detailed view of the left oxygen tube 20L forced into a curved shape by fasteners 17a-17d is shown in FIG. 2A. The fasteners 17a-17d cooperate with the attachments 12a-12d to hold the flaps in place on the headband 10a. The tube 12L is shown assuming a curved path through the fasteners 13a-13d. The curved path resists sliding the tube 20L, but allows a wearer to adjust the oxygen tubes for better comfort or fit. Adjacent fasteners 17a-17d are spaced apart by gaps G allowing the tube 20L to follow a curved path between the fasteners. The gaps G are greater than the diameter of the tube 20L to allow the tube 20L to pass between the fasteners 17a-17d.

Another embodiment of a headband 10b according to the present invention is shown in FIG. 3. The headband 10b includes a second flap 14b which is continuous (i.e., a continuous piece of material extending from the left rear to the front, and on to the right rear of the headband) and typically sewn into the headband 10b. Because the flap 14b is attached at a forward edge, three attachments 12a-12c are generally adequate to hold the flap 14b against the headband 10b and to force the oxygen tubes into a curved path and to allow the attachments to be detached and the flaps to be pulled away for placement of the tubes 20L and 20R behind the flaps. In this embodiment, the attachments 12a and 12b reside vertically spaced part at a rear edge of the flap 14b, and the attachment 12c resides horizontally spaced apart from the attachments 12a and 12b towards the front 15 of the headband 10b. The vertical separation of the attachments 12a and 12b help hold the end of the flap 14b in place and the attachment 14c is provided to allow the wearer to adjust the curved path of the tube 20L under the flap 14b. As in the headband 10a, the attachments are preferably snaps. The flap 10b may alternatively be two separate flaps sewn to the headband at a forward edge.

The flap may alternatively be permanently attached to the headband along a top, bottom, or rear edge and held in place by detachable attachments, for example, snaps, patches of Velcro® fastener material, or the like.

A cap 30 according to the present invention and including a headband carrying the tubes 20L and 20R is shown in FIG. 4. Oxygen tube wearers often desire to minimize the appearance of having to wear oxygen tubes, especially in the instance of a child wearer. The headbands of the present invention may be easily integrated into a cap, thus reducing the visibility of the oxygen tubes. The headband may be any headband having features to carry the oxygen tubes, but is particularly useful when a headband according to the present invention is included in the cap 30.

While the invention herein disclosed has been described by means of specific embodiments and applications thereof, numerous modifications and variations could be made thereto by those skilled in the art without departing from the scope of the invention set forth in the claims.

I claim:

1. Apparatus for carrying oxygen tubes for a personal oxygen supply, the apparatus comprising:
    a nasal cannula;
    a right oxygen tube connecting an oxygen source to the nasal cannula;
    a left oxygen tube connecting the oxygen source to the nasal cannula;
    a headband having a front and a rear and a headband interior surface; and
    flaps attachable inside the headband against the headband interior surface creating interior passages on each side of the headband between each flap and headband interior surface, each flap attached to the headband interior surface by at least three spaced apart detachable attachments, adjacent ones of the attachments separated by gaps to allow positioning the oxygen tubes between the attachments, each passage including:
        a tubing entry towards the rear of the headband;
        a tubing exit towards the front of the headband; and
        the attachments creating a curved path for the oxygen tubes through the passages, the curved paths for restricting movement of the oxygen tubes residing in the passages.

2. The apparatus of claim 1, wherein the attachments are spaced apart snaps.

3. The apparatus of claim 2, wherein the attachments are four spaced apart snaps residing at different heights on each flap.

4. The apparatus of claim 3, wherein the four spaced apart snaps comprise:
    a first snap positioned high and rearward on the flaps;
    a second snap positioned low and ahead of the first snap on the flaps;
    a third snap positioned at a medium height and ahead of the second snap on the flaps; and
    a fourth snap positioned high and forward on the flaps and ahead of the third snap.

5. The apparatus of claim 1, wherein the flaps are made of a material having approximately the same stretch as the headband to provide a comfortable fit.

6. The apparatus of claim 5, wherein the flaps are made of leather.

7. The apparatus of claim 1, wherein:
a sweatband is attached inside the front and side portions of the headband;
the flaps comprise end portions of the sweatband on each side portion and to the rear of the headband, the flaps being detachable from the headband;
the flaps include spaced apart attachments for attaching to the interior of the headband; and
the curved path is formed by routing the oxygen tubes around the attachments.

8. The apparatus of claim 1, wherein the headband is part of a cap.

9. Oxygen tubes for a personal oxygen supply and headwear for carrying oxygen tubes, the oxygen tubes and headwear comprising:
a nasal cannula;
a right oxygen tube connecting an oxygen source to the nasal cannula;
a left oxygen tube connecting the oxygen source to the nasal cannula;
a headband for residing around a wearer's head and having a headband front and a headband rear;
a right flap on a right inside rear portion of the headband;
a left flap on a left inside rear portion of the headband;
at least three snaps holding each flap in position;
a right path for the right oxygen tube under the right flap, the right path including a right tube entry towards the headband rear and a right tube exit towards the headband front; and
a left path for the left oxygen tube under the left flap, the left path including a left tube entry towards the headband rear and a left tube exit towards the headband front,
the snaps forcing the tubes to assume a curve along the paths, thereby holding the oxygen tubes.

10. Oxygen tubes for a personal oxygen supply and a cap for carrying the oxygen tubes, the oxygen tubes and cap comprising:
a cap top for covering a wearer's head;
a cap headband for carrying the cap on the wearer's head and having a headband front and a headband rear;
a nasal cannula;
a right oxygen tube connecting an oxygen source to the nasal cannula;
a left oxygen tube connecting the oxygen source to the nasal cannula;
a right flap on a right inside rear portion of the headband;
a left flap on a left inside rear portion of the headband;
at least three spaced apart snaps holding each flap in position; and
a right path for the right oxygen tube under the right flap, the right path including
a right tube entry towards the headband rear and a right tube exit towards the headband front; and
a left path for the left oxygen tube under the left flap, the left path including a left tube entry towards the headband rear and a left tube exit towards the headband front,
the snaps forcing the tubes to assume a curve along the paths, thereby holding the tubes.

* * * * *